United States Patent [19]

Ryan

[11] 4,395,560

[45] Jul. 26, 1983

[54] PREPARATION OF 6a,10a-TRANS-HEXAHYDRODIBEN-ZOPYRANONES

[75] Inventor: Charles W. Ryan, Indianapolis, Ind.

[73] Assignee: Eli Lilly and Company, Indianapolis, Ind.

[21] Appl. No.: 381,111

[22] Filed: May 24, 1982

[51] Int. Cl.³ .......................................... C07D 311/78
[52] U.S. Cl. .................................................. 549/391
[58] Field of Search ........................................ 549/391

[56] References Cited

U.S. PATENT DOCUMENTS

| 4,054,581 | 10/1977 | Blanchard et al. | 549/391 |
| 4,054,582 | 10/1977 | Blanchard et al. | 549/391 |
| 4,131,614 | 12/1978 | Ryan | 549/391 |
| 4,148,809 | 4/1979 | Day et al. | 549/391 |
| 4,171,315 | 10/1979 | Ryan | 549/391 |

Primary Examiner—Nicky Chan
Attorney, Agent, or Firm—Charles W. Ashbrook; Arthur R. Whale

[57] ABSTRACT

Reaction of an O-methyl or O-ethyl resorcinol with a cyclohexene carbinol derivative in the presence of a catalyst affords a 6a,10a-trans-1-methoxy or 1-ethoxy-6,6-dimethyl-6,6a,7,8,10,10a-hexahydro-9H-dibenzo[b,d]pyran-9-one derivative.

15 Claims, No Drawings

PREPARATION OF 6a,10a-TRANS-HEXAHYDRODIBENZOPYRANONES

BACKGROUND OF THE INVENTION

Certain 6a,10a-trans-hexahydrodibenzopyranones have recently been found useful in the treatment of anxiety, analgesia, and depression; see U.S. Pat. Nos. 3,928,598, 3,944,673, and 3,953,603 respectively. Archer et al., in U.S. Pat. No. 4,087,545, described the use of such compounds in the prevention and treatment of emesis and nausea in mammals. One compound within this class, namely dl-trans-1-hydroxy-3-(1,1-dimethylheptyl)-6,6-dimethyl-6,6a7,8,10,10a-hexahydro-9H-dibenzo[b,d]pyran-9-one, is now known generically as nabilone and is available in some countries as an antiemetic agent to be used in cancer chemotherapy, wherein cancer drugs often cause severe nausea.

The initial syntheses of hexahydrodibenzopyranones were quite lengthy and expensive, and generally led to hard to separate mixtures; see Fahrenholtz et al., *J. Am. Chem. Soc.*, 88, 2079 (1966); 89, 5934 (1967). These authors reported a synthesis that gave both the 6a,10a-cis isomers and 6a,10a-trans isomers. The cis isomers demonstrated little if any pharmacological activity, and were thus not claimed to have a utility, U.S. Pat. No. 3,507,885. Blanchard et al., in U.S. Pat. No. 4,054,582, disclosed a method for quantitatively converting the 6a,10a-cis isomers to the pharmacologically active 6a1-0a-trans isomers. Day et al., in U.S. Pat. No. 4,148,809, disclosed a convenient one step synthesis of the 6a,10a-cis compounds required in the Blanchard et al. process. This one step synthesis comprises condensing a 5-substituted resorcinol with a cyclohexene carbinol, namely a 1-alkoxy-4-(1-hydroxy-1-methylethyl)-1,4-cyclohexadiene, in the presence of a catalyst such as stannic chloride. Extensions of this process are described in U.S. Pat. No. 4,054,581 and 4,171,315.

I have now discovered that reaction of a protected resorcinol, for example a 3-alkoxy-5-substituted phenol, with a cyclohexene carbinol in the presence of a catalyst such as stannic chloride produces a 6a,10a-trans-hexahydrodibenzopyranone directly. An object of this invention thus is to provide a convenient one step synthesis of such 6a,10a-trans compounds.

SUMMARY OF THE INVENTION

This invention relates to a process for preparing 6a,10a-trans-hexahydrodibenzo[b,d]pyranones. The invention more particularly provides a one step process for preparing a 6a,10a-trans compound of the formula

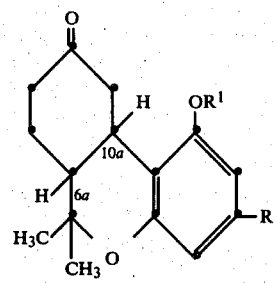

wherein R is $C_5$–$C_{10}$ alkyl, $C_5$–$C_{10}$ alkenyl, $C_5$–$C_8$ cycloalkyl or $C_5$–$C_8$ cycloalkenyl, and $R^1$ is methyl or ethyl; comprising reacting a 5-substituted resorcinol derivative of the formula

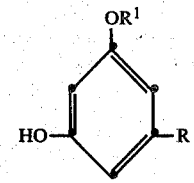

with a cyclohexene carbinol of the formula

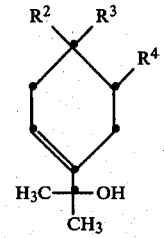

wherein $R^2$ is $C_1$–$C_4$ alkoxy and $R^3$ and $R^4$ together are a double bond, or $R^4$ is hydrogen and $R^2$ and $R^3$ together are oxo or a group of the formula

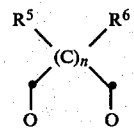

in which $R^5$ and $R^6$ independently are hydrogen, methyl or ethyl, and n is 0 or 1; in the presence of a catalyst selected from boron trifluoride, boron tribromide or stannic chloride.

The process is preferably carried out employing a resorcinol derivative wherein $R^1$ is methyl and a cyclohexene carbinol wherein $R^2$ is methoxy and $R^3$ and $R^4$ are a double bond. A preferred reaction catalyst is stannic chloride.

The process is most preferably carried out to prepare 6a,10a-trans dibenzopyranone derivatives defined by the above formula wherein R is $C_5$–$C_{10}$ alkyl, especially groups such as 1,1-dimethylheptyl, 1,2-dimethylheptyl and the like.

DETAILED DESCRIPTION OF THE INVENTION

The 6a,10a-trans-dibenzo[b,d]pyranones prepared by the method of this invention are substituted at the 3-position by a group defined as "R". This term refers to $C_5$–$C_{10}$ alkyl, $C_5$–$C_{10}$ alkenyl, $C_5$–$C_8$ cycloalkyl, and $C_5$–$C_8$ cycloalkenyl. When used herein, the term "$C_5$–$C_{10}$ alkyl" means both straight and branched carbon chains having from 5 to 10 carbon atoms. Examples of $C_5$–$C_{10}$ alkyl groups include n-pentyl, 1,1-dimethylpentyl, n-hexyl, n-octyl, isohexyl, 1-ethylhexyl, 1,2-dimethylheptyl, 1-ethyl-2-methylhexyl, 1,2,3-trimethylheptyl, 1-methylnonyl, n-decyl, and 1,1-dimethylheptyl. The term "$C_5$–$C_{10}$ alkenyl" means a straight or branched carbon chain of 5 to 10 carbon atoms and bearing one site of unsaturation. Typical $C_5$–$C_{10}$ alkenyl groups include 3-methyl-2-butenyl, 2-pentenyl, 1,2-dimethyl-1-hexenyl, 3-heptenyl, 1-ethyl-2-heptenyl, 1,1-dimethyl-2-octenyl, 3-nonenyl and related groups. R additionally defines a $C_5$–$C_8$ cycloalkyl group such as cyclopentyl, cyclohexyl, cycloheptyl or cyclooctyl, as well as a $C_5$–$C_8$ cycloalkenyl group such as 1-cyclopentenyl, 1-cyclohexenyl, 2-cycloheptenyl, 3-cyclooctenyl, and related cycloalkenyl groups.

The process of this invention requires as reactants a cyclohexene carbinol such as a 1-alkoxy-4-(1-hydroxy-1-methylethyl)-1,4-cyclohexadiene, and a protected resorcinol derivative. Preferred cyclohexene carbinols to be employed in the process are cyclohexadienes of the formula

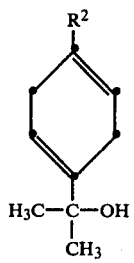

wherein $R^2$ is $C_1$–$C_4$ alkoxy. Typical cyclohexadienes that can be employed in the process include 1-methoxy-4-(1-hydroxy-1-methylethyl)-1,4-cyclohexadiene, 1-ethoxy-4-(1-hydroxy-1-methylethyl)-1,4-cyclohexadiene, 1-isopropoxy-4-(1-hydroxy-1-methylethyl)-1,4-cyclohexadiene and 1-n-butoxy-4-(1-hydroxy-1-methylethyl)-1,4-cyclohexadiene. These cyclohexadiene derivatives are readily prepared by reaction of a p-alkoxyacetophenone with a methyl Grignard reagent to give a 1-alkoxy-4-(1-hydroxy-1-methylethyl)-benzene, and then lithium reduction of the latter compound according to the procedure of Inhoffen et al., Ann. 674, 28–35 (1964).

Another preferred cyclohexene carbinol that can be employed in the present process is a cyclohexenone having the formula

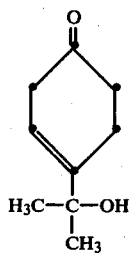

This cyclohexene carbinol is conveniently prepared by reaction of one of the above-mentioned cyclohexadienes, for instance 1-methoxy-4-(1-hydroxy-1-methylethyl)-1,4-cyclohexadiene, with an aqueous acid such as aqueous acetic acid.

Still other preferred cyclohexene carbinols that can be employed in the process of this invention include those of the formula

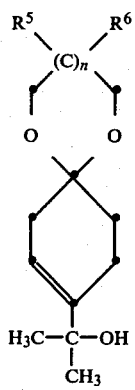

in which $R^5$ and $R^6$ independently are hydrogen, methyl or ethyl, and n is 0 or 1. These compounds are merely ketals of the aforementioned cyclohexenone reactant, and their synthesis is described in detail in U.S. Pat. No. 4,054,581. The portion of that patent describing the preparation of these ketals is incorporated herein by reference.

The protected resorcinol reactant required by the present process, i.e. a 3-methoxy or 3-ethoxy-5-substituted phenol, is readily prepared by procedures well known in the art. Typical protected resorcinols that can be employed in the present process include:
3-methoxy-5-n-pentylphenol;
3-ethoxy-5-n-octylphenol;
3-methoxy-5-n-decylphenol;
3-methoxy-5-(1,2-dimethylheptyl)phenol;
3-ethoxy-5-(1-ethylpentyl)phenol;
3-ethoxy-5-(1,1-dimethylhexyl)phenol;
3-methoxy-5-(3-hexenyl)phenol;
3-methoxy-5-(1,1-dimethyl-4-heptenyl)phenol;
3-ethoxy-5-(1-ethyl-5-octenyl)-phenol;
3-ethoxy-5-cyclohexylphenol;
3-ethoxy-5-cycloheptylphenol;
3-methoxy-5-cyclooctylphenol;
3-methoxy-5-(1-cyclohexenyl)phenol;
3-methoxy-5(2-cycloheptenyl)phenol; and
3-ethoxy-5-(3-cyclooctenyl)phenol.

The process provided by this invention is carried out by combining approximately equimolar quantities of a cyclohexene carbinol as defined above and a 3-methoxy or 3-ethoxy-5-substituted phenol, i.e. a protected resorcinol derivative as defined above. It is not essential to the process that these reactants be employed in equimolar quantities, and an excess of either reactant can be employed if desired. The reactants typically are combined in a mutual organic solvent such as chloroform, dichloromethane, ethyl acetate, acetone, benzene, toluene, or the like. The halogenated hydrocarbons such as dichloromethane are preferred reaction solvents. If desired, an equimolar or slight excess of water can be added to the reaction mixture. Addition of about an equimolar quantity of water to the reaction mixture, while not critical, appears to improve the yield of the desired product, presumably according to the mechanism involved in the process of U.S. Pat. No. 4,131,614. The reaction mixture generally is cooled to a temperature of about −30° to about 0° C., and then a reaction catalyst selected from stannic chloride, boron trifluoride or boron tribromide is added to the mixture, generally somewhat slowly in order to avoid a rapid rise in the reaction temperature. Boron trifluoride and boron tribromide typically are employed as the commercially available etherate complexes, for example boron trifluoride diethyl etherate and the like. The quantity of reaction catalyst employed can be about an equimolar quantity relative to the protected resorcinol reactant, but preferably is a slight excess, for example from about 0.1 to about 5.0 molar excess. Larger excesses are not detrimental to the reaction and can be employed if desired.

Following addition of the reaction catalyst, the reaction temperature generally rises rather quickly to about −10° to about 0° C. The reaction mixture can be stirred at this temperature for about 2 to about 24 hours. Ideally the temperature is permitted to rise slowly to about 25° C., and if desired the reaction mixture can be warmed to about 100° C. When carried out within the range of about −30° to about 100° C., the reaction generally is substantially complete within about 2 to about 24 hours, although longer reaction periods can be employed without adverse effects.

The progress of the reaction can be monitored by routine methods, for instance by thin layer chromatographic analysis. Once the reaction is substantially complete, the product can be readily isolated by simply washing the reaction mixture with water and then removing the reaction solvent, for example by evaporation under reduced pressure. The product is predominantly a 6a,10a-trans-1-methoxy or 1-ethoxy dibenzopyranone derivative, although a small amount of the corresponding 6a,10a-cis isomer may also be present. The amount of 6a,10a-cis isomer formed generally does not exceed about 5 to about 10 percent by weight of the reaction product. Any such cis isomer can be readily removed from the desired 6a,10a-trans isomer by routine purification techniques such as chromatography or crystallization. Alternatively, the product of the process can simply be treated with aluminum chloride according to the method of U.S. Pat. No. 4,054,582, thereby converting any cis isomer that might be present into the desired trans isomer.

It should be noted that the compounds produced by the process of this invention are racemic mixtures of optical isomers at the 6a and 10a positions. For example, a 6a,10a-trans dibenzopyranone produced by this invention will comprise a compound wherein the 6a hydrogen is $\beta$ and the 10a hydrogen is $\alpha$, plus the compound wherein the 6a hydrogen is $\alpha$ and the 10a hydrogen is $\beta$. Since both the d-6a,10a-trans and the l-6a,10a-trans optical isomers are equally useful, it is not necessary to separate these optical isomers. Accordingly, a preferred embodiment of this invention produces a dl-6a,10a-trans-1-methoxy or 1-ethoxy dibenzopyranone derivative.

The 6a,10a-trans-1-methoxy or 1-ethoxy compounds produced by the method of this invention are particularly useful as intermediates in the synthesis of 6a,10a-trans-1-hydroxy dibenzopyranones such as nabilone. Conversion of the 1-methoxy or 1-ethoxy derivatives to the corresponding 1-hydroxy compounds is accomplished by normal de-etherification procedures, for instance by reaction with reagents such as hydrobromic acid in acetic acid, pyridine hydrochloride, boron tribromide, aluminum chloride and the like. Such de-etherification reactions generally are carried out by combining the 1-methoxy or 1-ethoxy-6a,10a-trans-dibenzopyranone with an equimolar or excess amount of an agent such as boron trifluoride (typically as the diethyl etherate complex) in a mutual solvent such as chloroform, dichloromethane, dimethyl sulfoxide, or the like, and heating the reaction mixture at a temperature of about 30° to about 200° C. for about 6 to about 24 hours. The 6a,10a-trans-1-hydroxy dibenzopyranone that is formed is readily isolated by conventional means, for example by washing the reaction mixture with water and then removing the reaction solvent by evaporation. Further purification of the product can be accomplished by routine methods if desired, including chromatography and crystallization. The 6a,10a-trans-1-hydroxy dibenzopyranones thus produced are of significant value pharmacologically in the treatment of pain, depression, nausea and related maladies.

The following detailed examples will serve to more fully illustrate the process of this invention. The examples are not intended to limit the invention to the specific embodiments recited herein, and should not be so construed.

EXAMPLE 1 dl-trans-1-Methoxy-3-(1,1-dimethylheptyl)-6,6-dimethyl-6,6a,7,8,10,10a-hexahydro-9H-dibenzo[b,d]-pyran-9-one To a solution of 1.25 g (5 mM) of 3-methoxy-5-(1,1-dimethylheptyl)phenol in 25 ml of dichloromethane containing 1.008 g (6 mM) of 1-methoxy-4-(1-hydroxy-1-methylethyl)-1,4-cyclohexadiene were added 0.09 g (5 mM) of water. The reaction mixture was cooled to −20° C. and stirred while 1.25 ml of stannic chloride were added slowly over two minutes. The reaction mixture warmed to 0° C. and was stirred at that temperature for seven hours. The mixture was then washed three times with 10 ml portions of water; dried, and the solvent was removed by evaporation under reduced pressure to provide 1.93 g of an oil. The oil was purified by chromatography over 100 g of silica gel, eluting with toluene. Fractions 198–208 were collected, combined and the solvent was removed by evaporation to give 112 mg of dl-cis-1-methoxy-3-(1,1-dimethylheptyl)-6,6-dimethyl-6,6a,7,8,10,10a-hexahydro-9H-dibenzo[b,d]-pyran-9-one. Yield 5.8%. Fractions 184–192 were combined and the solvent was removed by evaporation to give 805 mg of dl-trans-1-methoxy-3-(1,1-dimethylheptyl)-6,6-dimethyl-6,6a,7,8,10,10a-hexahydro-9H-dibenzo[b,d]pyran-9-one. Yield 42%.

NMR (CDCl$_3$) consistent for 6a,10a-trans isomer.

$\delta$ 0.7–2.7 (m, 32H)
$\delta$ 1.1 (s, 3H, C$_6$ CH$_3$)
$\delta$ 1.5 (s, 3H, C$_6$ CH$_3$)
$\delta$ 3.8 (s, 3H, OCH$_3$)
$\delta$ 6.4 (m, 2H, aromatic)

EXAMPLE 2 dl-trans-1-Hydroxy-3-(1,1-dimethylheptyl)-6,6-dimethyl-6,6a7,8,10,10a-hexahydro-9H-dibenzo[b,d]pyran-9-one A solution of dl-trans-1-methoxy-3-(1,1-dimethylheptyl)-6,6-dimethyl-6,6a,7,8,10,10a-hexahydro-9H-dibenzo[b,d]pyran-9-one (prepared as described in Example 1) and boron tribromide in dichloromethane is stirred for about eight hours at about 40° C. The reaction mixture is then washed with water, dried, and the solvent is removed by evaporation under reduced pressure to give dl-trans-1-hydroxy-3-(1,1-dimethylheptyl)-6,6-dimethyl-6,6a,7,8,10,10a-hexahydro-9H-dibenzo[b,d]pyran-9-one. This compound is known as nabilone and is especially useful in the treatment of nausea in humans.

I claim:

1. A process for preparing a 6a,10a-trans compound of the formula

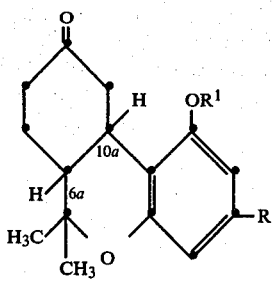

wherein R is $C_5$–$C_{10}$ alkyl, $C_5$–$C_{10}$ alkenyl, $C_5$–$C_8$ cycloalkyl or $C_5$–$C_{10}$ cycloalkenyl, and $R^1$ is methyl or ethyl; comprising reacting a 5-substituted resorcinol of the formula

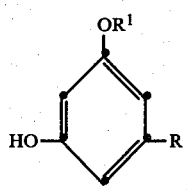

with a cyclohexene carbinol compound of the formula

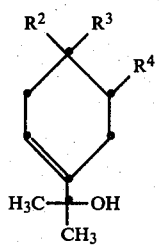

wherein $R^2$ is $C_1$–$C_4$ alkoxy and $R^3$ and $R^4$ together are a double bond, or $R^4$ is hydrogen and $R^2$ and $R^3$ together are oxo or a group of the formula

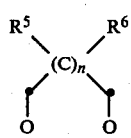

in which $R^5$ and $R^6$ independently are hydrogen, methyl or ethyl, and n is 0 or 1; in the presence of a catalyst selected from boron trifluoride, boron tribromide or stannic chloride.

2. The process of claim 1 employing a cyclohexene carbinol compound wherein $R^2$ is $C_1$–$C_4$ alkoxy and $R^3$ and $R^4$ together are a double bond.

3. The process of claim 2 employing a 5-substituted resorcinol wherein $R^1$ is methyl.

4. The process of claim 3 employing stannic chloride as catlayst.

5. The process of claim 4 employing a 5-substituted resorcinol wherein R is $C_5$–$C_{10}$ alkyl.

6. The process of claim 5 employing a 5-substituted resorcinol wherein R is 1,1-dimethylheptyl.

7. The process of claim 6 employing a cyclohexene carbinol wherein $R^2$ is methoxy.

8. The process of claim 1 employing a cyclohexene carbinol of the formula

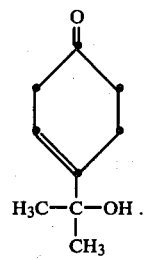

9. The process of claim 1 employing a cyclohexene carbinol of the formula

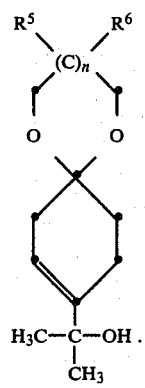

10. The process of claim 9 employing a cyclohexene carbinol wherein n is 0.

11. The process of claim 9 employing a cyclohexene carbinol wherein n is 1.

12. The process of claim 1 when carried out a temperature of about $-30°$ to about $100°$ C.

13. The process of claim 1 when carried out at a temperature of about $-20°$ to about $0°$ C.

14. The process of claim 1 when carried out in a halogenated hydrocarbon reaction solvent.

15. The process of claim 1 when carried out in the presence of about an equimolar quantity of water.

* * * * *